United States Patent [19] [11] 4,103,002
Hench et al. [45] Jul. 25, 1978

[54] BIOGLASS COATED A1203 CERAMICS

[75] Inventors: Larry Leroy Hench; David Charles Greenspan, both of Gainesville, Fla.

[73] Assignee: Board of Regents, University of Florida, Tallahassee, Fla.

[21] Appl. No.: 766,749

[22] Filed: Feb. 8, 1977

[51] Int. Cl.² .................. B32B 17/06; B32B 31/24; B32B 31/26
[52] U.S. Cl. .................. 428/155; 427/190; 427/257; 427/269; 427/279; 427/398 R; 428/426; 428/428; 428/432
[58] Field of Search .......... 106/47 R, 52, 54; 427/171, 257, 269, 279, 398 R, 402, 417, 190; 428/134, 135, 137, 155, 426, 432, 428, 539

[56] References Cited
U.S. PATENT DOCUMENTS

| | | | |
|---|---|---|---|
| 2,866,720 | 12/1958 | Martin et al. | 428/155 |
| 3,900,630 | 8/1975 | Makishima et al. | 428/155 |
| 3,934,961 | 1/1976 | Itch et al. | 428/432 X |

Primary Examiner—Thomas J. Herbert, Jr.
Assistant Examiner—R. Eugene Varndell, Jr.
Attorney, Agent, or Firm—Dennis P. Clarke

[57] ABSTRACT

A method of coating a $Al_2O_3$ ceramic surface with a biologically active glass comprising contacting a glass and ceramic having different thermal coefficients of expansion at a temperature sufficient to bond the glass to the ceramic surface by ion diffusion, cooling the coated substrate to a temperature sufficient to produce thermo-mechanical stress induced interconnected micro-cracks in the glass coating and overcoating said micro-cracked glass coating with at least one additional coating of biologically active glass. The invention includes a product of manufacture comprising a compacted $Al_2O_3$ ceramic surface coated with at least two layers of biologically active glass characterized in that the first layer of glass has interconnected thermo-mechanical stress induced micro-cracks therein.

20 Claims, 7 Drawing Figures

T > 500°C                              T = Room Temperature (20°C)
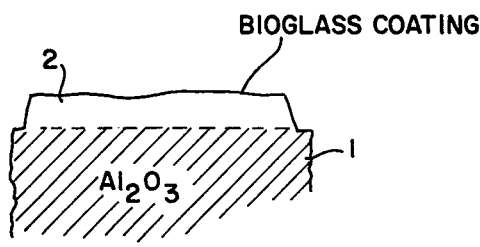
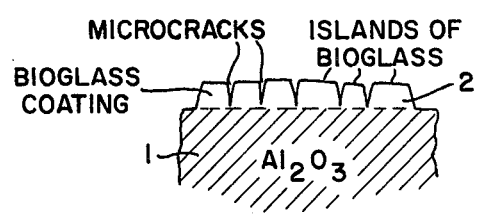
*Fig.5a*                                *Fig.5b*
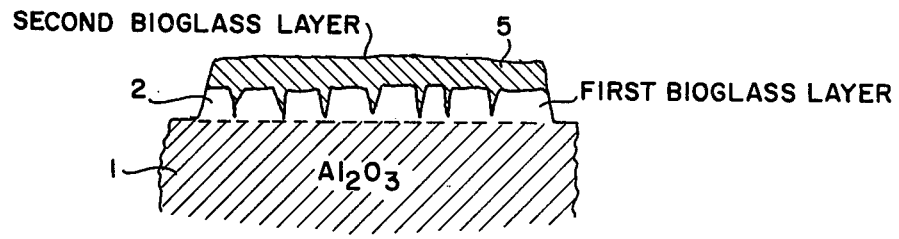
*Fig.5c*

BIOGLASS COATED Al2O3 CERAMICS

BACKGROUND OF THE INVENTION

The strength, anti-friction and high wear resistance properties of $Al_2O_3$ ceramics make them ideal for use in the construction of artificial protheses and orthopedic devices. The biological inactivity of $Al_2O_3$ ceramic surfaces, however, makes it extremely difficult, if not impossible, to achieve cement-free implantation of the prothesis since bone tissue will not bond or grow thereon.

Various techniques have recently been suggested for activating the ceramic surfaces in order to enhance the bone-tissue bonding capabilities of the $Al_2O_3$ prothesis. However, all of these techniques are either extremely expensive and time-consuming or result in ceramic structures of decreased mechanical strength, anti-friction properties and wear resistance.

It is an object of the present invention to provide a cement-free bone prothesis implant comprising a bioactive $Al_2O_3$ ceramic and a method for the preparation thereof which is inexpensive and does not result in a decrease of the mechanical strength, anti-friction and wear resistance properties of the $Al_2O_3$ ceramic material.

SUMMARY OF THE INVENTION

The present invention comprises a method of coating a compacted $Al_2O_3$ ceramic surface with a biologically active glass having a thermal coefficient of expansion different from that of the ceramic comprising:

1. Contacting the glass with the ceramic surface at a temperature and for a time sufficient to bond the glass to the ceramic surface by ion diffusion,
2. Cooling the coated substrate to a temperature sufficient to produce interconnected micro-cracks in the glass coating as a result of the thermo-mechanical stresses induced by the differential in thermal coefficients of expansion of said ceramic and glass, and,
3. Overcoating the micro-cracked glass coating with at least one additional coating of the biologically active glass.

The invention also relates to the product of the above-described process.

The biologically active glass coated compacted $Al_2O_3$ ceramic of the present invention comprises a ceramic surface coated with at least two layers of biologically active glass having a thermal coefficient of expansion different from that of the $Al_2O_3$ ceramic wherein the first layer is bonded to the ceramic surface by ion diffusion and is characterized by having interconnected thermo-mechanical stress induced microcracks therein and wherein the subsequent layer or layers are coated thereover.

The invention also relates to a cement-free bone prothesis implant comprising the above-described bioactive glass coated $Al_2O_3$ ceramic.

DETAILED DESCRIPTION OF THE INVENTION

Figure 1:
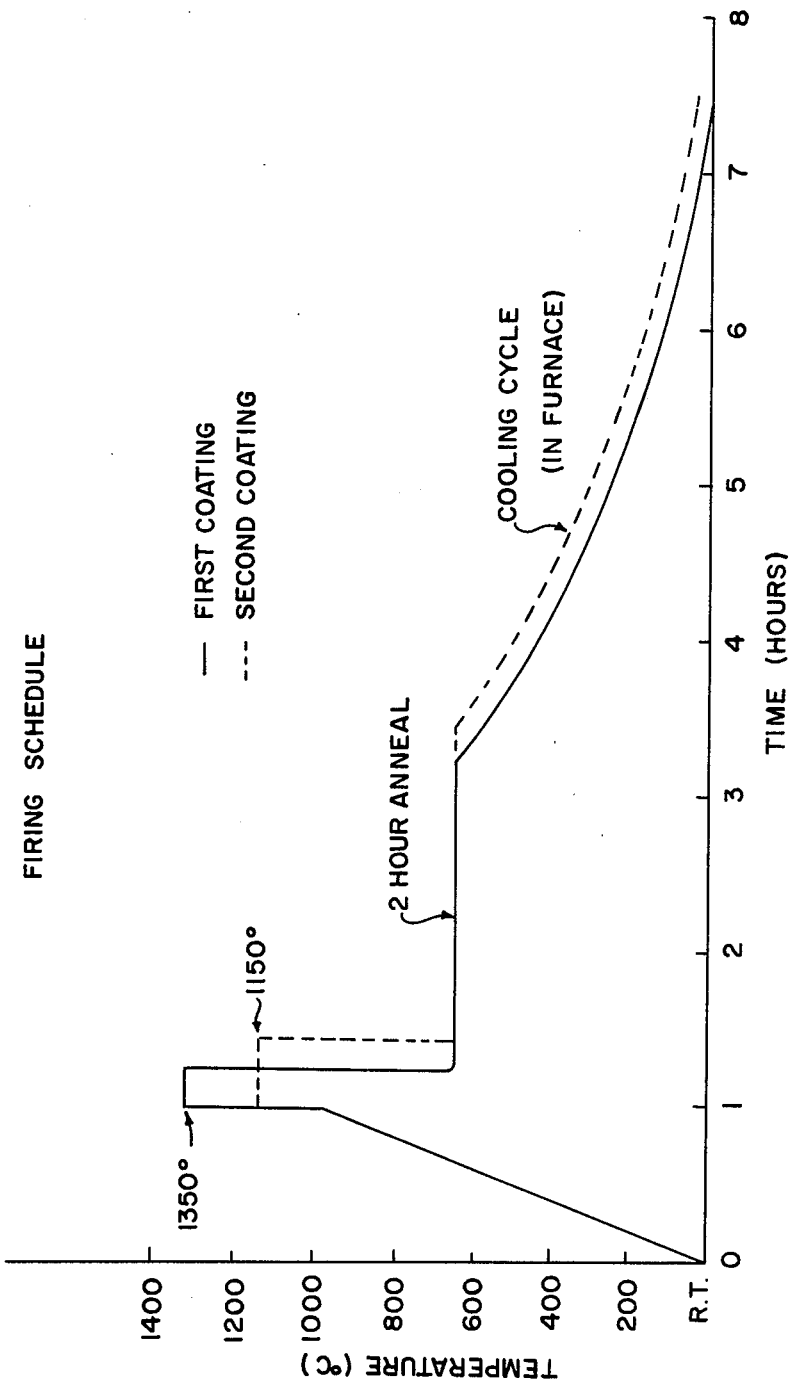

It is well known that when applying a glaze of higher thermal expansion to a body of lower thermal expansion, thermal stresses will arise upon cooling. Since these thermal stresses result in an overall weakening of the coated structure, it is conventional according to prior art practices to attempt to match the thermal coefficients of expansion of the respective materials as closely as possible in order to minimize these stresses. This necessarily results in a drastic reduction in the number and variety of coatings which can be applied to a particular substrate.

According to the present invention, extreme mismatches between the relative thermal coefficients of expansion are relied upon to induce thermo-mechanical stresses in the biologically active glass glaze coating. Upon cooling, the glaze cracks in order to relieve the stresses due to thermal mismatch, thereby resulting in isolated islands of biologically active glass coating separated by small interconnected flaws or micro-cracks. These cracks range from about 0.05 to 0.8 microns wide. The small islands of biologically active glass are bonded to the compacted $Al_2O_3$ ceramic surface by a large diffusional bond which is developed by processing at elevated temperatures (1100°–1350° C). The diffusional bond is a chemical bond between the $Al_2O_3$ substrate and the biologically active glass coating thereby eliminating a welldefined $Al_2O_3$-biologically active glass interface and results in an enhancement of the overall strength characteristics of the ceramic.

Multiple coatings of biologically active glass can then be applied over the micro-cracked glaze with no danger of inducing thermo-mechanical stresses in the structure. This is due to the fact that the second and subsequent glass layers are bonded to the first biologically active glass layer and not to the $Al_2O_3$ substrate. Thus, the second glass layer has physical properties identical to the first glass layer with no mismatch in the respective coefficients of thermal expansion.

The resulting structure has the capacity to bond living tissues to an implant material comprised of the coated ceramic substrate due to the properties of the biologically active glass. In addition, the coating process does not deleteriously affect the mechanical strength of the $Al_2O_3$ ceramic since all thermo-mechanical stresses are relieved during the first coating operation and no further stresses are induced by the second and subsequent glass coating steps.

Since no regard need be given to the thermal coefficient of expansion match, a wider variety of biologically active glass materials can be coated upon the ceramic surface than by the techniques presently prevalent in the prior art.

Indeed, by carefully controlling the coating procedure, the strength of the compacted $Al_2O_3$ ceramic can actually be enhanced. By maintaining the size of the flaws or micro-cracks at below 1 micron, the strength and fatigue resistance of the $Al_2O_3$ ceramic is increased.

Any biologically active glass may be employed for the purposes of the present invention. It will be understood by those skilled in the art that any suitable biologically active glass, depending upon the ultimate use for which the coated ceramic is intended, may be utilized. Generally, the biologically active glass is one capable of bonding to living tissue and contains, by weight:

$SiO_2$ — 40– 62%
$Na_2O$ — 10– 32%
$CaO$ — 10– 32%
$P_2O_5$ — 3– 9%
$CaF_2$ — 0– 18%
$B_2O_3$ — 0– 7.5%

$Na_2O$ + $CaO$ must be above 30% to achieve bonding to live tissue.

Suitable specific glasses include those of the following compositions:

A.

SiO$_2$ — 45.0%
Na$_2$O — 24.5%
CaO — 24.5%
P$_2$O$_5$ — 6.0%

B.

SiO$_2$ — 42.94%
Na$_2$O — 23.37%
CaO — 11.69%
P$_2$O$_5$ — 5.72%
CaF$_2$ — 16.26%

C.

SiO$_2$ — 40.0%
Na$_2$O — 24.5%
CaO — 24.5%
P$_2$O$_5$ — 6.0%
B$_2$O$_3$ — 5.0%

In order to achieve the micro-cracked glass coating, it is generally preferred to employ a compacted Al$_2$O$_3$ ceramic having a thermal coefficient of expansion (0°–1,000° C) in the range 35–75 × 10$^{-7}$ in/in/° C. and a biologically active glass having a thermal coefficient of expansion (0°–1,000° C.) in the range 95–145 × 10$^{-7}$ in/in/° C.

The biologically active glasses are first melted (e.g., in platinum crucibles) for 3–12 hours to insure homogeneity. The melting temperatures range from about 1300° C. to about 1550° C. After melting, the biologically active glass is quenched in water and ground in a ball mill into glass frit of the desired particle size. Generally, a particle size of less than about 74 microns is preferred. The frit is then mixed with an organic binder (e.g., organic polymers such as a mixture of 20% polyvinylacetate and 80% polyvinylalcohol) and a suitable organic solvent (e.g., toluene, acetone, xylene, etc.) to form a slurry. The amount of binder used depends upon the particle size of the frit employed. Generally, larger particles require greater amounts of binder to achieve adequate coverage. The amount of solvent employed is varied to control the viscosity of the slurry and the thickness of the ultimate coating. Generally, the slurry will contain from about 35 to about 80 percent glass frit, from about 1 to about 10 percent binder, and from about 20 to about 65 percent organic solvent, all percentages being by weight.

The compacted Al$_2$O$_3$ substrate to be coated is then dipped into the slurry or the slurry is handpainted or sprayed onto the substrate. The coating is allowed to dry thoroughly.

The coated substrate is then fired following a schedule that will allow burn-off of the organic binder, followed by a softening of the glass and subsequent bonding of the glass to the substrate by ion diffusion. The high alkali content of the biologically active glass is one of the major factors that allows for good diffusional bonding between the coating and the substrate. The coated glass is then annealed to relieve mechanical stresses.

Employing the biologically active glass composition A described above and a compacted Al$_2$O$_3$ ceramic having a thermal coefficient of expansion of 50–75 × 10$^{-7}$ in/in° C., the firing schedule set forth in FIG. 1 was employed. Although FIG. 1 sets forth a double coated structure, it will be understood by those skilled in the art that successive coats of biologically active glass may be applied thereover following the same firing schedule, depending upon the desired surface properties of the resulting coated system. The biologically active glass glaze ultimately coated upon the compacted Al$_2$O$_3$ ceramic surface contains 0.475 moles of Na$_2$O, 0.525 moles CaO, 0.050 moles P$_2$O$_5$, and 0.900 moles SiO$_2$ (normalized with respect to alkali content).

The combination of (1) composition of the glasses (high alkali, low silica) which allows for relatively high diffusion rates and (2) the various time-temperature firing schedules which control the amount of diffusion permit the controlled micro-cracking of the base coat of biologically active glass. The control of these two variables also permits regulation of the diffusion bonding which is ultimately responsible for the success of the coated system.

The temperature to which the coated system is subjected to achieve ion diffusion bonding depends, of course, on the particular glass and Al$_2$O$_3$ ceramic compositions employed. Generally, temperatures above 500° C, preferably in the range of 900° to 1400° C, and most preferably from 1100° to 1350° C, are utilized.

The first coat is applied such that the ultimate thickness thereof is from about 25–100 microns. Subsequent coatings may range from about 50 to about 400 microns.

Figure 2:
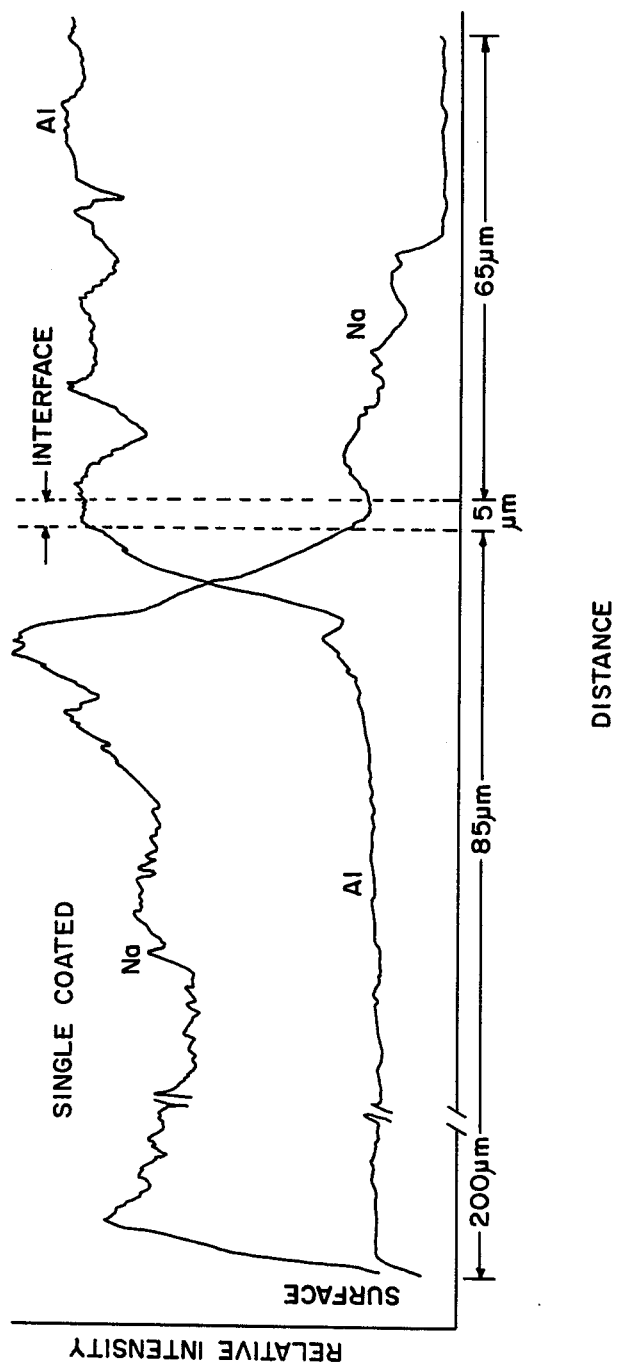

FIG. 2 sets forth an electron micro probe scan of sodium and aluminum in the single coated structure set forth above. The degree of diffusional bonding is apparent from the fact that alumina is found as far into the glass as 200 microns.

Figure 3:
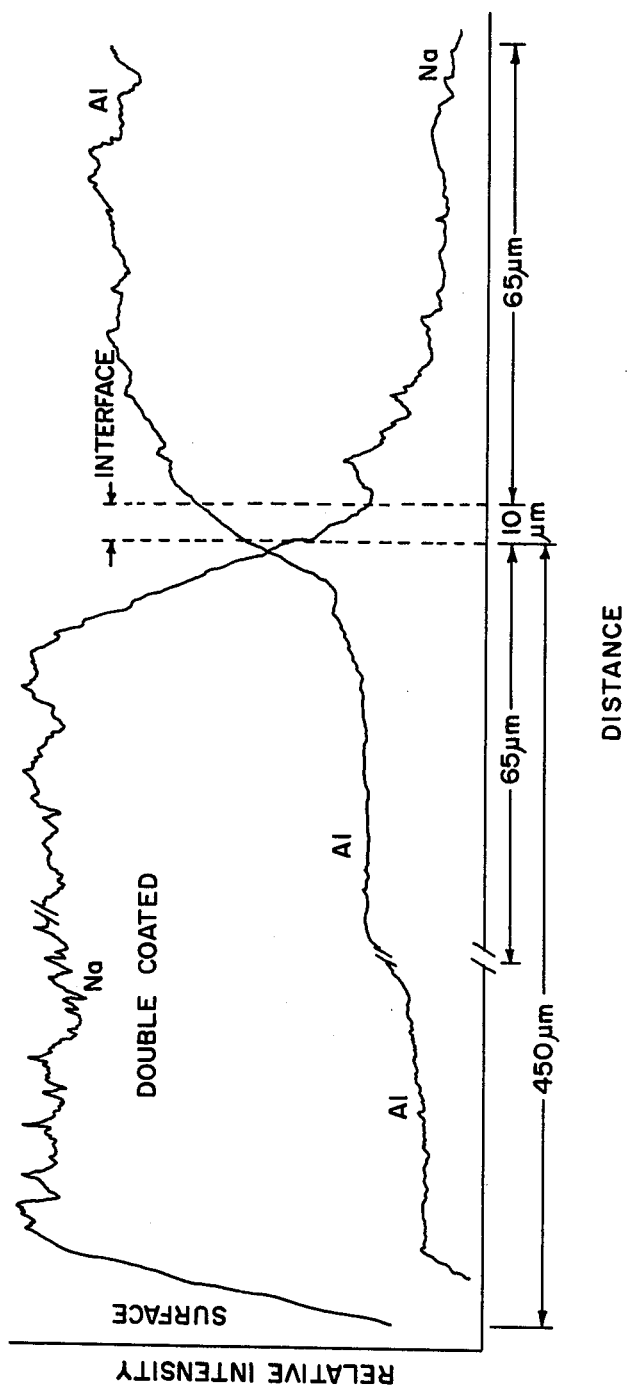

FIG. 3 sets forth an electron micro probe scan of sodium and aluminum in the above-described double coated system. The fact that the second coating is largely bonded to the first glass coating is apparent from the decreased intensity of the alumina signal in the second layer of the glass coating.

Figure 4:
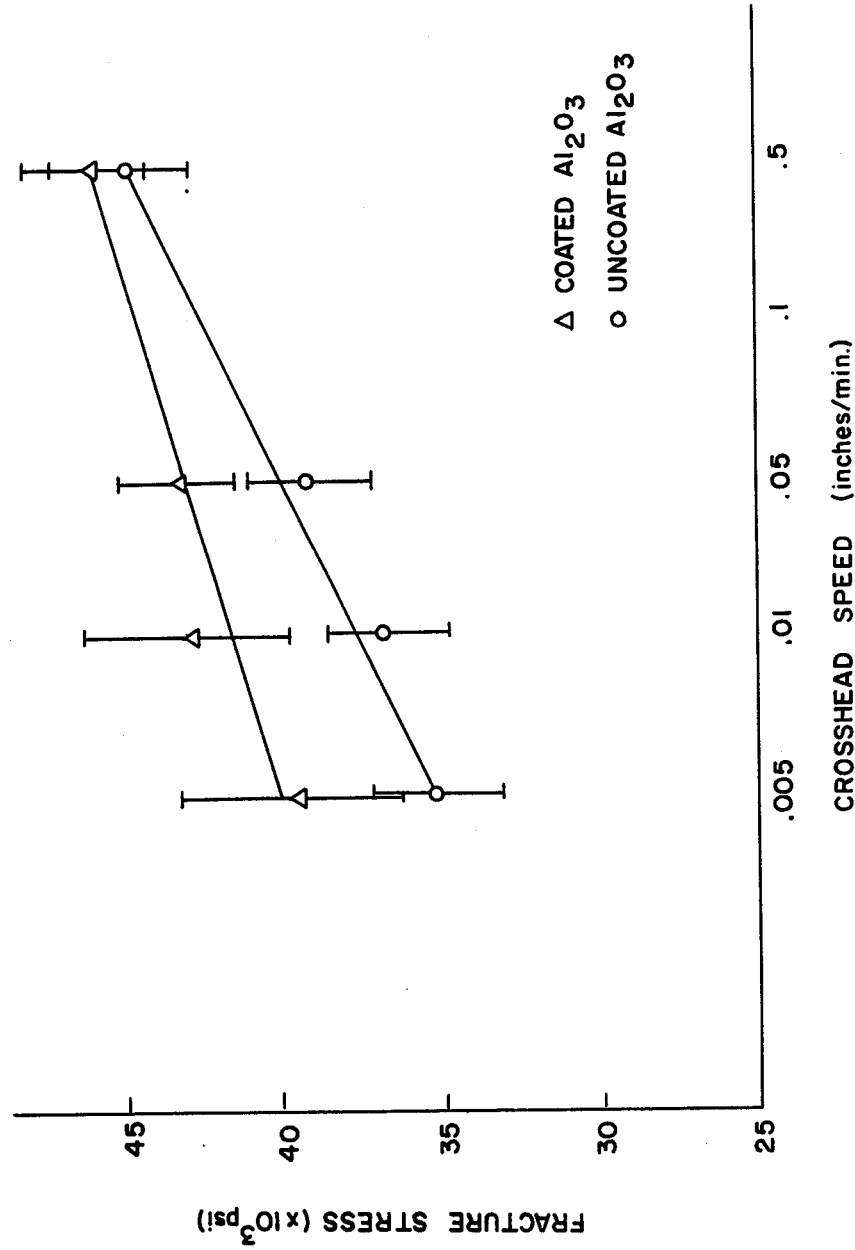

FIG. 4 sets forth the strain rate dependence of the biologically active glass coated vs. uncoated Al$_2$O$_3$ surface. It is apparent that the fatigue resistance of the coated material is greater as compared with the uncoated substrate.

As noted above, the application of a glaze of higher thermal expansion on a body of lower thermal expansion will result in thermal stresses upon cooling. These stresses can be calculated employing the following equation:

$$\sigma gl = E(T_o - T')(\alpha gl - \alpha_b)(1 - 3j + 6j^2)$$

where j = glaze thickness/body thickness
$\alpha gl$ = thermal expansion of glaze
E = Youngs modulus
$\alpha_b$ = thermal expansion of body
$T_o$ = annealing temperature of glaze
$\sigma g'$ = thermal stress (psi)
T = final temperature [room temp. (20° C)]

In the above-described example employing composition A:

j = 0.02
T° = 450° C
E = 8 × 10$^6$
T' = 20° C
$\alpha gl$ = 100 × 10$^{-7}$ in/in/° C
$\alpha b$ = 50 × 10$^{-7}$ in/in/° C Substituting these parameters into the above equation, the thermal stress is found to be 8.2 × 10$^{-3}$ psi. It is, therefore, apparent that the degree of micro cracking can be calculated, depending upon the particular compositions employed and the firing, coating and annealing schedules followed.

FIG. 5 sets forth the coated ceramic substrate in various stages of formation.

In FIG. 5a, wherein the temperature is greater than 500° C., the ceramic substrate 1 is overcoated with the first layer of biologically active glass 2.

In FIG. 5b, wherein the system has been cooled to room temperature, micro-cracks 3 appear in the coating 2 forming islands 4 of biologically active glass bonded, by ion diffusion, to the ceramic substrate 1.

FIG. 5c depicts a micro-cracked biologically active glass coated $Al_2O_3$ ceramic substrate overcoated with a second biologically active glass layer 5.

The thus coated $Al_2O_3$ ceramic substrates are ideally adapted for the formation of cement-free bone prothesis implants of unusually high strength and capable of forming bonds with biologically active tissue.

What is claimed is:

1. A method of coating a compacted $Al_2O_3$ ceramic surface with a biologically active glass, said ceramic and glass having different thermal coefficients of expansion, comprising:
   (1) contacting said glass with said ceramic surface at a temperature and for a time sufficient to bond said glass to said ceramic surface by ion diffusion,
   (2) cooling said coated substrate to a temperature sufficient to produce interconnected micro-cracks in said glass coating as a result of the thermo-mechanical stresses induced by the differential in thermal coefficients of expansion of said ceramic and glass, and
   (3) overcoating said micro-cracked glass coating with at least one additional coating of biologically active glass.

2. The method of claim 1 wherein said biologically active glass contains, by weight:
   $SiO_2$ — 40–62%
   $Na_2O$ — 10–32%
   $CaO$ — 10–32%
   $P_2O_5$ — 3–9%
   $CaF_2$ — 0–18%
   $B_2O_3$ — 0–7.5%

3. The method of claim 1 wherein said biologically active glass contains, by weight:
   $SiO_2$ — 45.0%
   $Na_2O$ — 24.5%
   $CaO$ — 24.5%
   $P_2O_5$ — 6.0%

4. The method of claim 1 wherein said biologically active glass contains, by weight:
   $SiO_2$ — 42.94%
   $Na_2O$ — 23.37%
   $CaO$ — 11.69%
   $P_2O_5$ — 5.72%
   $CaF_2$ — 16.26%

5. The method of claim 1 wherein said biologically active glass contains, by weight:
   $SiO_2$ — 40.0%
   $Na_2O$ — 24.5%
   $CaO$ — 24.5%
   $P_2O_5$ — 6.0%
   $B_2O_3$ — 5.0%

6. The method of claim 1 wherein said ceramic surface has a thermal coefficient of expansion (0°–1,000° C.) in the range 50–75 × $10^{-7}$ in/in/° C. and said glass has a thermal coefficient of expansion (0°–1,000° C.) in the range 95–145 × $10^{-7}$ in/in/° C.

7. The method of claim 1 wherein each of said coatings is annealed.

8. The method of claim 1 wherein said glass is bonded to said ceramic surface at a temperature above 500° C.

9. The method of claim 1 wherein said glass coated ceramic surface is cooled so as to produce micro-cracks in said glass coating having a width less than 1 μm.

10. The product of the process of claim 1.

11. A cement-free bone prothesis implant comprising the product of the process of claim 1.

12. The method of claim 1 wherein said glass is contacted with said ceramic surface by coating said ceramic surface with a slurry comprising a solvent, an orgnic binder, and a biologically active glass frit having a particle size less than 74 μm.

13. The method of claim 12 including the steps of drying the slurry coated ceramic substrate and firing the coated substrate to burn off said organic binder.

14. A product of manufacture comprising a compacted $Al_2O_3$ ceramic surface coated with at least two layers of biologically active glass having a thermal coefficient of expansion different from that of said $Al_2O_3$ ceramic, said first layer being bonded to said ceramic surface through ion-diffusion and characterized by having interconnected thermo-mechanical stress induced micro-cracks therein, and said subsequent layer or layers being successively bonded thereover.

15. The product of claim 14 wherein said biologically active glass contains, by weight:
   $SiO_2$ — 40 – 62%
   $Na_2O$ — 10 – 32%
   $CaO$ — 10 – 32%
   $P_2O_5$ — 3 – 9%
   $CaF_2$ — 0 – 18%
   $B_2O_3$ — 0 – 7.5%

16. The product of claim 14 wherein said biologically active glass contains, by weight:
   $SiO_2$ — 45.0%
   $Na_2O$ — 24.5%
   $CaO$ — 24.5%
   $P_2O_5$ — 6.0%

17. The product of claim 14 wherein said bilogically active contains, by weight:
   $SiO_2$ — 42.94%
   $Na_2O$ — 23.37%
   $CaO$ — 11.69%
   $P_2O_5$ — 5.72%
   $CaF_2$ — 16.26%

18. The product of claim 14 wherein said bilogically active glass contains, by weight:
   $SiO_2$ — 40.0%
   $Na_2O$ — 24.5%
   $CaO$ — 24.5%
   $P_2O_5$ — 6.0%
   $B_2O_3$ — 5.0%

19. The product of claim 14 wherein said ceramic surface has a thermal coefficient of expansion (0°–1,000° C.) in the range 50–75 × $10^{-7}$ in/in/° C. and said glass has a thermal coefficient of expansion (0°–1,000° C.) in the range 95–145 × $10^{-7}$ in/in/° C.

20. A cement-free bone prothesis implant comprising the product of claim 14.

* * * * *

UNITED STATES PATENT AND TRADEMARK OFFICE
CERTIFICATE OF CORRECTION

PATENT NO. : 4,103,002
DATED : July 25, 1978
INVENTOR(S) : LARRY LEROY HENCH, DAVID CHARLES GREENSPAN It is certified that error appears in the above-identified patent and that said Letters Patent are hereby corrected as shown below:

Column 1, after title "BIOGLASS COATED $Al_2O_3$ CERAMICS", insert --The invention described herein was made in the course of work under a grant or award from the Department of Health, Education, and Welfare".

Signed and Sealed this

Eleventh Day of December 1979

[SEAL]

Attest:

SIDNEY A. DIAMOND

Attesting Officer        Commissioner of Patents and Trademarks